(12) United States Patent
Fang et al.

(10) Patent No.: US 6,821,982 B2
(45) Date of Patent: Nov. 23, 2004

(54) PREPARATION OF A CAMPTOTHECIN DERIVATIVE BY INTRAMOLECULAR CYCLISATION

(75) Inventors: Francis Gerard Fang, Durham, NC (US); Edward McDonald Huie, Cary, NC (US); Shiping Xie, Cary, NC (US); Daniel L. Comins, Raleigh, NC (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 10/395,806

(22) Filed: Mar. 24, 2003

(65) Prior Publication Data

US 2003/0204088 A1 Oct. 30, 2003

Related U.S. Application Data

(63) Continuation of application No. 10/243,470, filed on Sep. 13, 2002, now Pat. No. 6,559,309, which is a division of application No. 09/552,214, filed on Apr. 19, 2000, now Pat. No. 6,462,196, which is a continuation of application No. 08/737,032, filed as application No. PCT/US95/05427 on May 2, 1995, now Pat. No. 6,063,923.

(51) Int. Cl.$^7$ ..................... A61K 31/436; C07D 519/00
(52) U.S. Cl. ......................................... 514/291; 546/83
(58) Field of Search ............................. 514/291; 546/83

(56) References Cited

U.S. PATENT DOCUMENTS

| | | |
|---|---|---|
| 4,399,276 A | 8/1983 | Miyasaka et al. |
| 4,399,282 A | 8/1983 | Miyasaka et al. |
| 4,413,118 A | 11/1983 | Roberts et al. |
| 4,473,692 A | 9/1984 | Miyasaka et al. |
| 4,545,880 A | 10/1985 | Miyasaka et al. |
| 4,778,891 A | 10/1988 | Tagawa et al. |
| 4,871,855 A | 10/1989 | Marko et al. |
| 4,894,456 A | 1/1990 | Wall et al. |
| 4,943,579 A | 7/1990 | Vishnuvajjala et al. |
| 4,965,364 A | 10/1990 | Marko et al. |
| 4,981,968 A | 1/1991 | Wall et al. |
| 5,049,668 A | 9/1991 | Wall et al. |
| 5,053,512 A | 10/1991 | Wani et al. |
| 5,106,742 A | 4/1992 | Wall et al. |
| 5,122,526 A | 6/1992 | Wall et al. |
| 5,122,606 A | 6/1992 | Wani et al. |
| 5,126,494 A | 6/1992 | Gilheany et al. |
| 5,162,532 A | 11/1992 | Comins et al. |
| 5,180,722 A | 1/1993 | Wall et al. |
| 5,191,082 A | 3/1993 | Comins et al. |
| 5,200,524 A | 4/1993 | Comins et al. |
| 5,212,317 A | 5/1993 | Comins et al. |
| 5,227,380 A | 7/1993 | Wall et al. |
| 5,227,543 A | 7/1993 | Sharpless et al. |
| 5,243,050 A | 9/1993 | Comins et al. |
| 5,244,903 A | 9/1993 | Wall et al. |
| 5,247,089 A | 9/1993 | Comins et al. |
| 5,254,690 A | 10/1993 | Comins et al. |
| 5,258,516 A | 11/1993 | Comins et al. |
| 5,260,461 A | 11/1993 | Hartung et al. |
| 5,264,579 A | 11/1993 | Comins et al. |
| 5,315,007 A | 5/1994 | Comins et al. |
| 5,321,140 A | 6/1994 | Comins et al. |
| 5,340,817 A | 8/1994 | Wall et al. |
| 5,342,947 A | 8/1994 | Lackey et al. |
| 5,364,858 A | 11/1994 | Wall et al. |
| 5,395,939 A | 3/1995 | Comins |
| 5,428,166 A | 6/1995 | Comins |
| 5,438,132 A | 8/1995 | Bray et al. |
| 5,475,108 A | 12/1995 | Comins et al. |
| 5,491,237 A | 2/1996 | Fang et al. |
| 5,559,235 A | 9/1996 | Luzzio et al. |
| 6,063,923 A | 5/2000 | Fang et al. |
| 6,284,891 B1 | 9/2001 | Fang et al. |
| 6,462,196 B1 | 10/2002 | Fang et al. |

FOREIGN PATENT DOCUMENTS

| | | |
|---|---|---|
| DD | DD 0152774 | 12/1981 |
| EP | 0321122 | 6/1989 |
| EP | 0325247 | 7/1989 |
| EP | 0418099 | 3/1991 |
| EP | 0429963 | 5/1991 |
| EP | 0540099 | 5/1993 |
| EP | 0556585 | 8/1993 |
| JP | 63014824 | 1/1988 |
| WO | WO 8906225 | 7/1989 |
| WO | WO 9105556 | 5/1991 |
| WO | WO 9116322 | 10/1991 |
| WO | WO 9207856 | 5/1992 |
| WO | WO 9211263 | 7/1992 |
| WO | WO 9220677 | 11/1992 |
| WO | WO 9307142 | 4/1993 |
| WO | WO 9316698 | 9/1993 |
| WO | WO 9411377 | 11/1993 |
| WO | WO 9325556 | 12/1993 |
| WO | WO 9404160 | 3/1994 |
| WO | WO 9425466 | 11/1994 |
| WO | WO 97/00876 | * 1/1997 |

OTHER PUBLICATIONS

Berry, D.E. et al., (1992) "Naturally Occurring Inhibitors of Topoisomerase 1 Mediated DNA Relaxation" *J. Org. Chem.*, 57:420–422.

(List continued on next page.)

*Primary Examiner*—Rita Desai
(74) *Attorney, Agent, or Firm*—Cooper & Dunham LLP

(57) ABSTRACT

The present invention relates to a method for the preparation for camptothecin and camptothecin-like compounds and to novel intermediates used in this preparation. In particular, the invention provides a process for the preparation of the camptothecin derivative of formula (I') known by the chemical name "7-(4-methylpiperazino-methylene)-10,11-ethylenedioxy-20(R,S)-camptothecin", which comprises cyclising the compound of formula (II'), wherein X is halogen, particularly chloro, bromo, or iodo; and when the compound of formula (I') is obtained as a mixture of enantiomers optionally resolving the mixture to obtain the desired enantiomer; and/or if desired, converting the resulting compound of formula (I') or a salt thereof into a physiologically acceptable salt or solvate thereof.

5 Claims, No Drawings

OTHER PUBLICATIONS

Comins, D. L., (1977) "The Synthesis of Analogs of Camptothecin" A thesis submitted to the University of New Hampshire.

Comins, D.L. et al., (1992) "A 10-step, Asymmetric Synthesis of (S)-camptothecin", *Journal of the American Chemical Scoiety*, 114:10971–10972.

Comins, D.L. et al., (1994) "A Six-step Synthesis of (+) camptothecin", *Journal of Organic Chemistry*, 59:5120–5121.

Comins, D.L. et al., (1994) "Asymmetric Synthesis of Camptothecin alkaloids: A Nine-Step Synthesis of (S)-camptothecin," *Tetrahedron Letters* 35:5331–5334.

Corey, E.J. et al., (1975) "A Total Synthesis of Natural 20 (S–)-Camptothecin", *J. Org. Chem.*, 40:2140–2141.

Curran D.P. et al., (1992) "New 4 + 1 Radical Annulations. A Formal Total Synthesis of (±)-Camptothecin", *J. Am. Chem. Soc.*, 114:5863–5864.

Crispino, G.A. et al., (1993) "Improved Enantioselectivity in Asymmetric Dihydroxylations of Terminal Olefins Using Pyrimidine Ligands", *J. Org. Chem.*, 58:3785–3786.

Eckardt, J.R. et al., (1993) "Topoisomerase J Inhibitors: Promising Novel Compounds", *Contemporary Oncology*, 47–60.

Ejima, A. et al., (1989) "Asymmetric Synthesis of (S)-Camptothecin", *Tetrahedron Letters*, 30:2639–2640.

Earl, R.A. et al., (1984) "The Preparation of 2(1H)-Pyridinones and 2, 3-Dihydro-5(1H)-indolizinones via Transition Metal Mediated Cyclization of Alkynes and Isocyanates. A Novel Construction of the Antitumor Agent Camptothecin", *J. Org. Chem.*, 49:4786–4800.

"Enantioselective Formal Synthesis of 20(S)-Camptothecin: An Application of the Sharpless Asymmetric Dihydroxylation Reaction", Department of Synthetic Organic chemistry, Glaxo Inc., Research Triangle Park, NC 27709.

Fang, F.G. et al. (1994) "Catalytic Enantioselective Synthesis of 20(S)-camptothecin: A Practical Application of the Sharpless Asymmetric Dihydroxylation Reaction," *J. Org. Chem.*, 59:6142–6143.

Fang, F.G. et al. (1997) "Convergent catalytic Asymmetric Synthesis of Camptothecin Analog G1147211C".

Grieco, P.A. et al., (1976) "Remote Double Bond Migration via Rhodium Catalysis: A Novel Enone Transposition" *J. Am. Chem. Soc.*, 98:7102–7104.

Grigg, R. et al., (1990) "The Synthesis of Fused Ring Nitrogen Heterocycles Via Regionspecific Intramolecular Heck Reactions[1]", *Tetrahedron Letters.* 46:4003–4018.

Heck, R.F., (1987) "Double Bond Isomerazation" *Palladium Reagents in Organic Syntheses*, Academic Press Inc., San Diego, CA Chapter 2.

Herzberg, R.P. (1989) "Modification of the Hydroxy Lactone Ring of Camptothecin," *J. Med. Chem.* 32(3):715–720.

Kingsbury, W.D., (1988) "The Chemical Rearrangement of Camptothecin to Mappicine Ketone", *Tetrahedron Letters* 29:6847–6850.

Kingsbury, W.D. et al., (1991) "Synthesis of Water-Soluble (Aminoalkyl) camptothecin Analogues: Inhibition of Topoisomerase I and Antitumor Activity", *J. Med. Chem.*, 34:98–107.

Klibanov, A.M., (1990) "Asymmetric Transformations Catalyzed by Enzymes in Organic Solvents" *Acc. Chem. Res.*, 23:114–120.

U.S. patent application Ser. No. 10/243,470, Fang et al., filed Sep. 13, 2002.

Larock, R.C. , (1989) "Alkene and Alkyne Additions", *Comprehensive Organic Transformations: A guide to Functional Group Preparations*, VCH Publications, New York Chapter 4.

Meyers, A.I. et al., (1973) "A Total Synthesis of Camptothecin and Deethyldeoxycamptothecin", *J. Org. Chem.*, 38:1974–1982.

Quick, J., (1977) "A New Route to Pyridones Via Imines of Pyruvic Esters", *Tetrahedron Letters*, 4:327–330.

Sugasawa, T. et al., (1979) "Aminohaloborane in Organic Synthesis.2. Simple Synthesis of Indoles and 1-Acyl-3-indolinones Using Specific Ortho α-Chloroacetylation of Anilines", *J. Org. Chem.*, 44:578–586.

Sugasawa, T. et al., (1972) "A Total Synthesis of dl-Camptothecin", *Tetrahedron Letters*, 50:5109–5112.

Wani, M.C. et al., (1980) "Plant Antitumor Agnets. 18.[1] Synthesis and Biological Activity of Camptothecin Analogues", *J. Med. Chem.*, 23:554–560.

Wani, M.C. et al., (1972) "Plant Antitumor Agents. I.X The Total Synthesis of dl–Camptothecin", *J. Am. Chem. Soc.*, 94:3631–3632.

Wani, MC. et al., (1986) "Plant Antitumor Agents. 23.[1] Synthesis and Antileukemic Activity of Camptothecin Analogues", *J. Med. Chem.*, 29:2358–2363.

Wani, M.C. et al., (1987) "Plant Antitumor Agents. 28. Resolution of a Key Tricyclic Synthon, 5' (RS)–1, 5-Dioxo-5'ethyl-5'-hydroxy-2'H,5',6'H-6'-oxopyrano [3', 4'-f] $\Delta^{6,8}$ -tetrahydroindolizine: Total Synthesis and Antitumor Activity of 20(S)-and 20(R)-Camptothecin," *J.Med. Chem.*, 30:2317–2319.

International Search Report for International Application No. PCT/US95/05427.

International Search Report for International Application No. PCT/US95/05425.

International Preliminary Examination Report for International Application No. PCT/US95/05427; and.

International Preliminary Examination Report for International Application No. PCT/US95/05425.

* cited by examiner

PREPARATION OF A CAMPTOTHECIN DERIVATIVE BY INTRAMOLECULAR CYCLISATION

This application is a continuation of U.S. Ser. No. 10/243,470, filed Sep. 13, 2002, now U.S. Pat. No. 6,559,309 which is a divisional of U.S. Ser. No. 09/552,214, filed Apr. 19, 2000, now U.S. Pat. No. 6,462,196, issued Oct. 8, 2002, which is a continuation of U.S. Ser. No. 08/737,032, filed Nov. 1, 1996, now U.S. Pat. No. 6,063,923 issued May 16, 2000, which is a §371 of PCT International Application No. PCT/US95/05427, filed on May 2, 1995, claiming priority of U.S. Ser. No. 08/237,081, filed May 3, 1994, now U.S. Pat. No. 5,491,237 issued Feb. 16, 1996.

FIELD OF THE INVENTION

The present invention relates to a method for the preparation of camptothecin and camptothecin-like compounds and to novel intermediates used in this preparation.

BACKGROUND OF THE INVENTION

Camptothecin and many camptothecin-like compounds, i.e., derivatives have been found to have potent cytotoxicity, and hence, are potent antitumor agents. The camptothecin moiety common to these compounds has a chiral center at the 20 position. The configuration about this position appears to be important to the antitumor activity of camptothecin and its derivatives now in clinical trials.

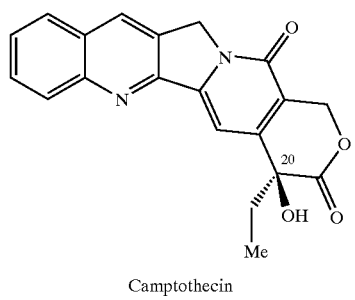

Camptothecin

Camptothecin and its derivatives can be produced using several processes taught in the art such as those described in U.S. Pat. Nos. 4,894,456; 4,399,282, 4,399,276; 4,943,579; European Patent Application 0 321 122 A2 published Jun. 21, 1989; U.S. Pat. No. 4,473,692, European Patent application No. 0 325 247 A2 published Jul. 26, 1989; European Patent application 0 556 585 A2 published Aug. 25, 1993; U.S. Pat. Nos. 4,981,968; 5,049,668; 5,162,532; 5,180,722; and European Patent application 0 540 099 A1 published May 5, 1993.

SUMMARY OF THE INVENTION

One aspect of the present invention is the preparation of the camptothecin derivative of formula (I')

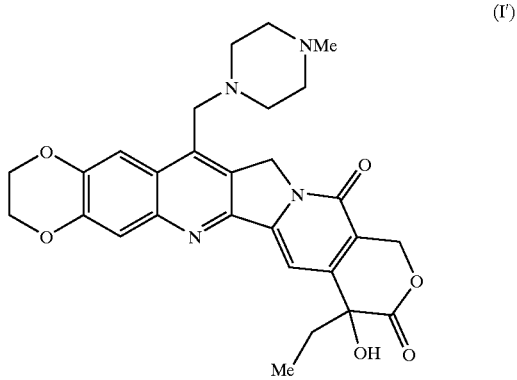

known by the chemical name "7-(4-methylpiperazino-methylene)-10,11-ethylenedioxy-20(R,S)-camptothecin," which comprises cyclising the compound of formula (II")

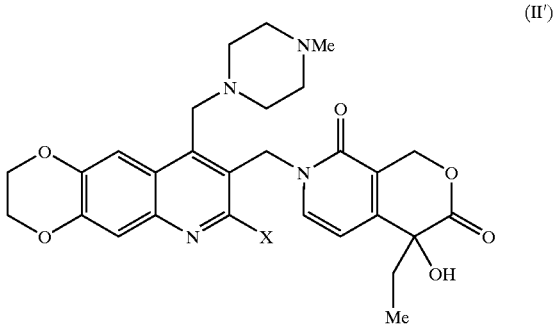

wherein X is halogen, particularly chloro, bromo, or iodo.

A particular aspect the invention provides a process for preparing a compound of formula (I) as shown in Scheme 1 wherein the configuration about the 20 position is (S)

Scheme 1

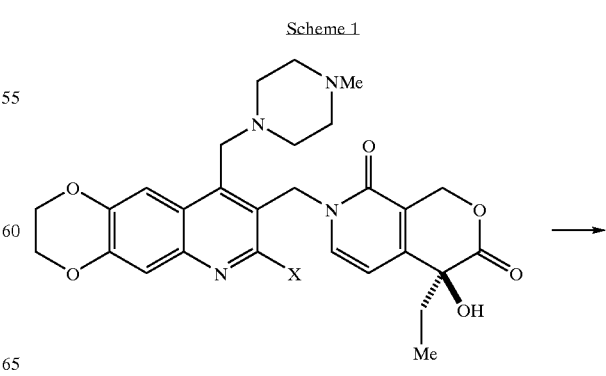

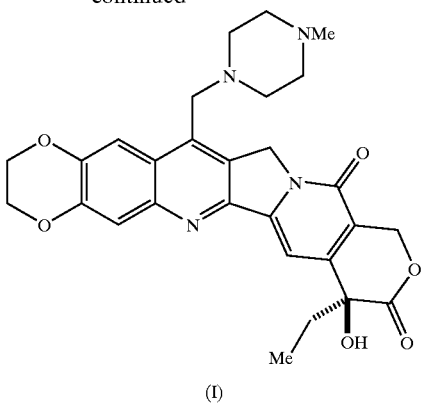

(I)

Further aspects of the present invention provide the intermediate of formula (II'), particularly of formula (II), and novel intermediates used in the synthesis of the compounds of formula (II') and (II) taught herein.

DETAILED DESCRIPTION OF THE INVENTION

Compounds of the present invention have 1 or more asymmetric carbon atoms that form enantiomeric arrangements, i.e., "R" and "S" configurations. The present invention includes all enantiomeric forms and any combinations of these forms. For simplicity, where no specific configuration is depicted in the structural formulas, it is to be understood that both enantiomeric forms and mixtures thereof are represented. Unless noted otherwise, the nomenclature convention, "(R)" and "(S)" denote essentially optically pure R and S enantiomers respectively. Also included in the present invention are other forms of the compounds including: solvates, hydrates, various polymorphs and the like.

Acceptable salts include, but are not limited to acid addition salts of inorganic acids such as hydrochloride, sulfate, phosphate, diphosphate, hydrobromide, and nitrate; or of organic acids such as acetate, malate, maleate, fumarate. tartrate, succinate, citrate, lactate, methanesulfonate, p-toluenesulfonate, palmoate, salicylate, oxalate, and stearate. Also within the scope of the present invention, where applicable, are salts formed from bases such as sodium or potassium hydroxide. For further examples of physiologically acceptable salts see, "Pharmaceutical Salts," *J. Pharm. Sci.*, 66 (1), 1 (1977).

The cyclisation process to prepare the compound of formula (I') from a compound of formula (II')via the intramolecular Heck may be carried out in the presence of a palladium catalyst such as palladium(II) acetate under basic conditions, e.g., in the presence of an alkaline earth carbonate, such as potassium carbonate in a polar, aprotic solvent, e.g., acetonitrile or dimethylformamide.

A phase transfer catalyst such as a tetraalkylammonium halide salt , e.g., tetra-n-butyl ammonium chloride, tetra-n-butyl ammonium bromide, or tetra-n-butyl ammonium iodide, may optionally be included. A ligand for the palladium catalyst may also be included such as a triphenylphosphine, tri-o-tolyphosphine, tri-m-tolyphosphine or tri-p-tolyphosphine. In particular, the reaction may be carried out in an inert atmosphere, such as under nitrogen or argon. Suitably, the reaction mixture is heated, for example to a temperature between about 50° to about 110° C. for about 1 to about 24 hours. Variations on these conditions will be apparent from the literature on the Heck reaction. See, e.g., R. Grigg et al., *Tetrahedron* 46, 4003–4008 (1990).

Alternatively, the cyclisation process may be accomplished by a free-radical cyclisation reaction. Suitably, the reaction is carried out in a solvent such as toluene in the presence of a tin hydride, e.g., tri-n-butyltin hydride, and a radical initiator at an elevated temperature e.g. of from about 50° C. to about 100° C.

When the compound of formula (I') is obtained as a mixture of enantiomers, the cyclisation process may optionally be followed by a resolution step, using conventional technology known in the art, to obtain the desired enantiomer. Furthermore, when the compound of formula (I') is obtained as a free base or a salt thereof, the cyclisation process may optionally be followed by a conversion step whereby the resulting compound of formula (I') is converted into a physiologically acceptable salt or solvate thereof.

The compound of formula (II) may be prepared according to Scheme 2.

Scheme 2

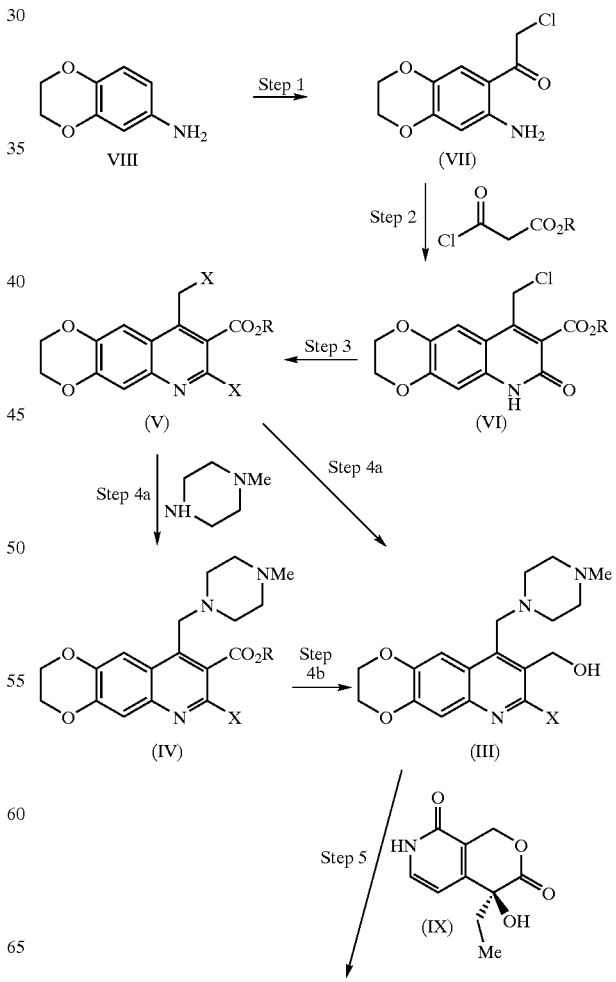

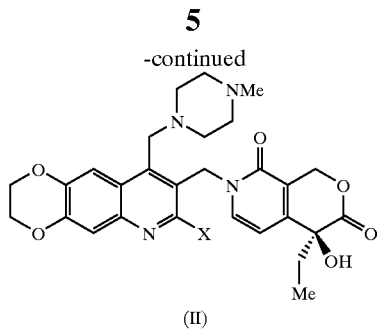

(II)

In Step 1 of Scheme 2 a compound of formula (VIII), 1,4-benzodioxan-6-amine, commercially available from the Aldrich Chemical Company, Inc., 1001 West Saint Paul Avenue, Milwaukee, Wis. 53233, is acylated in a Friedel-Crafts Acylation adding a halomethylketone to the 6 position producing the halo-ketone of formula (VII) (see March, *Advanced Organic Chemistry*, 484–487, 496–97 (1985)). The acylation can be carried out in a halogenated solvent such as dichloromethane in the presence of a Lewis acid such as boron trichloride, an acylating agent such as chloroacetonitrile, and another Lewis acid such as aluminum chloride or gallium chloride. The mixture is heated at a temperature of from about 30 to about 40° C. To those skilled in this art, variations on these conditions will be apparent from the literature on Friedel-Crafts Acylation of anilines.

In Step 2, the halo-ketone of formula (VII) is reacted in a two-step, single vessel reaction (N-acylation followed by base-mediated Aldol condensation) producing the halomethylquinolone of formula (VI). The reaction is carried out in a polar, aprotic solvent such as acetonitrile in the presence of a suitable base such as triethylamine and an acylating agent such as an alkyl malonyl chloride, e.g., ethyl malonyl chloride, at a temperature ranging from about 0° C. to about 30° C., followed by the addition of more base such as sodium methoxide in methanol or triethylamine.

In Step 3, the halomethyl-quinolone of formula (VI) is converted to a haloquinoline of formula (V) using a halogenating reagent such as phosphorus oxychloride or phosphorus oxybromide. The reaction is carried out in the presence of the halogenating reagent and may use an additional cosolvent such as 1,2-dichloroethane at a temperature ranging from about 50° C. to about 120° C. for about 2 to about 24 hours.

In Step 4, the compound of formula (V) is transformed into the compound of formula (III) by a two-step process which may involve separate isolation of the intermediate compound of formula (IV). The compound of formula (V) is dissolved in an aprotic solvent such as dichloromethane or tetrahydrofuran and treated with N-methylpiperazine in the presence of an amine base such as triethylamine or N-methylpiperazine at a temperature of from about room temperature to about 80° C. for about 1 to 12 hours. The intermediate compound of formula (IV) may be isolated at this point. In particular, the reaction solvent may be exchanged it necessary for dichloromethane and a reducing agent such as an aluminum hydride, e.g. diisobutylaluminum hydride, is added at a temperature ranging from about room temperature (20° C.–30° C.) to about 37° C. with stirring for about 1 to 12 hours.

In step 5, the compound of formula (III) is reacted with a compound of formula (IX) to give the compound of formula (II) using a Mitsunobu reaction (see O. Mitsunobu et al., *Synthesis* 1 (1981)). This reaction is carried out by adding a dialkylazodicarboxylate, e.g. diethylazodicarboxylate or diisopropylazodicarboxylate, to a mixture of the pyridone of formula (IX) (see Scheme 3 below) and the alcohol of formula (III), and a triaryl- or trialkylphosphine, such as triphenylphosphine or tributylphosphine in an aprotic solvent, e.g., 1,2-dimethoxyethane, tetrahydrofuran, toluene, acetonitrile, ethyl acetate, acetone, chloroform, methyl tert-butyl ether, dimethylformamide, or particularly dichloro-methane, at a temperature ranging from about 0° C. to about 40° C. for about 1 to about 12 hours. Variation on these conditions will be apparent from the literature on the Mitsunobu reaction.

Mixtures of enantiomers of formula (II') may be prepared in an analogous manner and may be used to prepare mixtures of enantiomers of formula (I'). Alternatively, if desired, the mixtures of enantiomers of formula (II') may be resolved to provide a compound of formula (II) before cyclising to provide a compound of formula (I) as shown in Scheme 1.

The compound of formula (IX) may be prepared by the process of Scheme 3:

Scheme 3

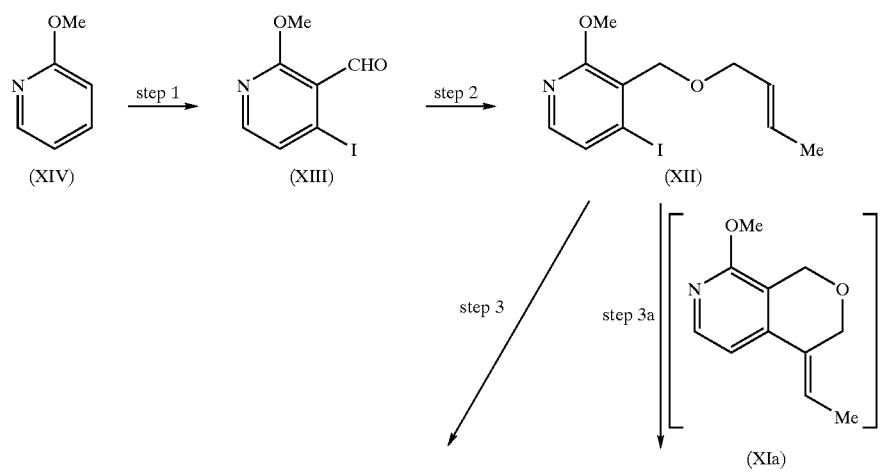

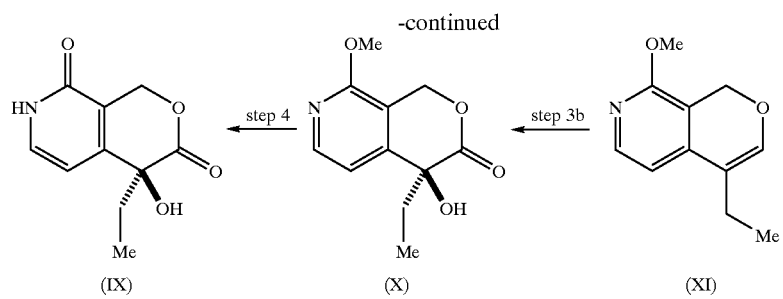

In Step 1 of Scheme 3, the compound of formula (XIV), 2-methoxypyridine, available from the Aldrich Chemical Company, Inc., 1001 West Saint Paul Avenue, Milwaukee, Wis. 53233, is sequentially formylated and halogenated to yield the halopyridinecarboxaldehyde of formula (XIII). The formylation may be carried out by deprotonation at the 3-position of the pyridine ring with a base such as tert-butyllithium in a mixture of an ether solvent such as tetrahydrofuran or 1,2-dimethoxyethane, and a hydrocarbon solvent such as pentane or heptane at a temperature ranging from about −78° C. to about −60° C. The C-3 lithiated pyridine intermediate is then alkylated with a formylating agent such as N-formyl-N,N',N'-trimethylethylenediamine at a temperature ranging from about −60° C. to about −10° C. The intermediate aminoalkoxy species is further deprotonated at the C-4 position using a base such as n-butyllithium. The C-4 lithiated pyridine intermediate can then be halogenated by mixing the intermediate with a solution of iodine or bromine in a polar or non-polar, organic solvent, in particular at a temperature ranging from about −78° C. to about −45° C. See D. Comins and M. Killpack, J. Org. Chem., 55, 68–73 (1990).

In step 2, the compound of formula (XIII) is reduced then alkylated to give an ether of formula (XII). The reaction is carried out in a protic acid such as trifluoroacetic acid in the presence of an alcohol such as crotyl alcohol and a reducing agent such as a trialkylsilane, e.g., trimethylsilane or triethylsilane, at a temperature ranging from about 0° C. to about 30° C. Alternatively, the reaction may be carried out in an ether solvent such as tetrahydrofuran in the presence of a reducing agent such as sodium borohydride and an alcohol such as methanol at a temperature ranging from about 0° C. to about 30° C. followed by addition of a base such as an amide base, e g., lithium hexamethyldisilazide, and an alkylating agent such as crotyl bromide at a temperature ranging from about 0° C. to about 30° C.

The transformation of step 3 may be carried out in two stages, i.e., steps 3a and 3b. In step 3a the compound of formula (XII) may be cyclized by an intramolecular Heck reaction to form the compound of formula (XI). The reaction may be carried out in the presence of a palladium catalyst, e.g., palladium acetate, under basic conditions in a polar, aprotic solvent, e.g., acetonitrile or dimethylformamide) or a polar, protic solvent, e.g., n-propanol, i-propanol, or t-butanol. A phase transfer catalyst such as a tetraalkylammonium halide salt, e.g., tetrabutylammonium chloride, tetrabutylammonium bromide or tetrabutylammonium iodide may be included especially when a polar, aprotic solvent is used. A ligand for the palladium catalyst may also be included such as a triphenylphosphine, tri-o-tolylphosphine, tri-m-tolylphosphine, or tri-p-tolylphosphine. An isomerization catalyst, e.g., tris (triphenylphosphine)rhodium(I) chloride, may also be included. The reaction should be carried out in an inert atmosphere, such as under nitrogen or argon gas at a temperature ranging from about 50° C. to about 110° C. for about 1 to about 24 hours. The intermediate of formula (XIa) may be isolated but this is not necessary. Variations on these conditions will be apparent from the literature on the Heck reaction. See, e.g., R. Grigg et al. Tetrahedron 46, 4003–4008 (1990).

In step 3b, the compound of formula (XI) may be transformed to the compound of formula (X) by i) dihydroxylation using a catalytic asymmetric dihydroxylation and ii) oxidation of the resultant diol. The dihydroxylation reaction is carried out in the presence of an osmium catalyst, e.g., potassium osmate (VI) dihydrate, osmic chloride hydrate or osmium tetroxide, a chiral tertiary amine catalyst, e.g., derivatives of the cinchona alkaloids such as 2,5-diphenyl-4,6-bis(9-O-dihydroquinidyl)pyrimidine, a stoichiometric oxidizing reagent, e.g., potassium ferri-cyanide, hydrogen peroxide or N-methylmorpholine N-oxide, and a primary amide, e.g., methanesulfonamide, under basic conditions, e.g., in the presence of potassium carbonate, in an aqueous mixture containing a polar protic solvent, e.g., t-butanol, i-propanol, n-propanol. The reaction can be carried out a a temperature ranging from about 0 to about 25° C. for about 48 hours. See K B. Sharpless, et al., J. Org. Chem. 58, 3785–3786 (1993). The oxidation of the intermediate diol can be carried out in the presence of an oxidizing reagent, e.g., iodine, in a polar, protic medium, e.g., aqueous methanol, aqueous tert-butanol or aqueous n-propanol, in the presence of a base, e.g., calcium-carbonate, at a temperature ranging from about 0° C. to about 25° C.

In step 4, the methoxypyridine of formula (X) may be converted to the pyridone of formula (IX) in a polar, protic solvent, e.g., water, in the presence of a protic acid, e.g., hydrochloric acid, at a temperature ranging from about 25° C. to about 100° C. for about 1 to about 6 hours. Alternatively, the conversion of (X) to (IX) may be carried out in a polar, aprotic solvent such as acetonitrile in the presence of a trialkylsilylhalide, e.g., trimethylsilyliodide, at a temperature ranging from about 25° C. to about 85° C. for about 1 to about 24 hours.

EXAMPLES

The following examples illustrate various aspects of the present invention, but should not be construed as limitations. The symbols, conventions and nomenclature not specifically defined below are consistent with those used in the contemporary chemical literature, for example the Journal of the American Chemical Society.

Unless otherwise noted all starting materials were obtained from commercial suppliers and used without further purification. All reactions involving oxygen or moisture-sensitive compounds were performed under a dry $N_2$ atmosphere.

Intermediate 1
4-Iodo-2-methoxy-pyridine-3-carbaldehyde (Formula (XIII))

A 5 liter 3-necked round bottom flask is equipped with an overhead mechanical stirrer under nitrogen, the flask is charged with tetrahydrofuran (1 L) and cooled to −78° C. To this stirred solution is added tert-butyllithium (1.7 M in pentane, 800 mL, 1.36 mol) via canula followed by 2-methoxypyridine (132.2 g, 1.21 mol) at −78° C. The mixture is allowed to stir for one hour at −78° C. To the mixture is added N-formyl-N,N',N'-trimethylethylenediamine (176 mL, 1.37 mol) dropwise at −78° C. described as in Comins, D. L.; Baevsky, M. F.; Hong, H. *J. Am. Chem. Soc.* 1992, 114, 10972. The reaction mixture is stirred for about 30 min at −78° C. before warming to −23° C. over about 30 min. To the mixture at −23° C. is added ethylene glycol dimethyl ether (1 L) followed by n-butyllithium (2.5 M in hexanes, 800 mL, 2.0 mol). The resultant mixture is stirred for about 2 hours during which time the reaction mixture turns deep green. A 12 liter 4-neck round bottom flask is equipped with an overhead mechanical stirrer under nitrogen, the 12 liter flask is charged with iodine (571 g, 2.25 mol) and ethylene glycol dimethyl ether (2 L) and the resultant solution is cooled to −78° C. The contents of the 5 liter flask are transferred via canula to the mixture of iodine and ethylene glycol dimethyl ether in the 12 liter flask at −78° C. After the addition is complete, the reaction mixture is stirred for an additional 1 hour at −78° C. The cooling bath is removed and the mixture is allowed to warm to about −0° C. then treated with 2 L of water and 2 L of 1N hydrochloric acid. Methyl t-butyl ether (2 L) is added and the layers are separated. The aqueous layer is extracted with 2×1 L of methyl t-butyl ether. The combined organic extracts are washed with 1.2 L of saturated sodium thiosulfate solution followed by 1.2 L of saturated sodium chloride solution. The organic extracts are dried over sodium sulfate, filtered, and concentrated in vacuo to give a thick slurry. To the slurry is added 1 L of hexane resulting in the generation of additional precipitate. The mixture is cooled in an ice/water bath for about 30 min then filtered yielding 4-iodo-2-methoxypyridine-3-carbaldehyde. The filtrate is reconcentrated to a slurry and treated with hexane to generate additional precipitate again yielding 4-iodo-2-methoxypyridine-3-carbaldehyde. Chromatography (silica gel, 10% ethyl acetate/hexane) yields an analytical sample as a bright yellow solid: mp 98–99° C. 1H-NMR (400 MHz, CDCl$_3$) 10.21 (s, 1H), 7.86 (d, J=5 Hz, 1H), 7.54 (d, J=5 Hz, 1H), 4.06 (s, 3H); IR (CHCl$_3$) 1710, 1560, 1470, 1380, 1305, 1260, 1025 cm$^{-1}$; Elemental analysis: calculated for $C_7H_6NO_2I$: C 31.97%, H 2.30, N 5.32, I 48.25; Found: C 32.06, H 2.35; N 5.25, I 48.35.

Intermediate 2
3-(But-2-enyloxymethyl)-4-iodo-2-methoxy-pyridine (Formula (XII))

A 500 mL 3-necked round-bottom flask is equipped with an overhead mechanical stirrer under nitrogen, the flask is charged with 4-iodo-2-methoxy-pyridine-3-carbaldehyde (Intermediate 1, 75.0 g, 0.29 mol), crotyl alcohol (75 mL, 0.88 mol), and triethylsilane (70 mL, 0.44 mol). To the stirred suspension at 0° C. is added trifluoroacetic acid (175 mL, 2.27 mol) dropwise via an addition funnel. The resulting solution is stirred at about 22° C. for approximately 12 hours. The reaction mixture is slowly poured into a rapidly stirring saturated sodium bicarbonate solution (2 L). The mixture is extracted with 3×500 mL of hexane. The combined organic layers are dried over sodium sulfate, filtered, and concentrated in vacuo to give an oil. Purification of this oil by vacuum distillation (about 0.4 mm Hg, about 120–130° C.) yields 3-(but-2-enyloxymethyl)-4-iodo-2-methoxypyridine as a pale yellow oil: $^1$H-NMR (400 MHz, CDCl$_3$) d 7.69 (d, J=5 Hz, 1H), 7.34 (d, J=5 Hz, 1H), 5.71 (m, 2H), 4.58 (s, 2H), 4.02 (d, J=1 Hz, 2H), 3.94 (s, 3H), 1.72 (d, J=6 Hz, 3H); IR (neat) 2948, 2859, 1561, 1459, 1381, 1361, 1301, 1233, 1169, 1094, 1052 cm$^{-1}$; Elemental analysis: calculated for $C_{11}H_{14}NO_2I$: C 41.40, H 4.42, N 4.39, I 39.76; Found: C 41.31, H 4.45, N 4.37, I 39.71.

Intermediate 3
a) 4-Ethylidene-8-methoxy-3,4-dihydro-1H-pyrano[3,4-c] pyridine (Formula (XIa)): b) 4-Ethyl-8-methoxy-1H-pyrano [3,4-c]pyridine (Formula (XI)); c) 3(R)-4(S)-4-ethyl-8-methoxy-3,4-dihydro-1H-pyrano[3,4-c]pyridine-3,4-diol; d) 4(S)-4-ethyl-4-hydroxy-8-methoxy-1,4-dihydro-pyrano[3,4-c]pyridin-3-one (Formula (X))

A 5 liter 3-necked round bottom flask is equipped with an overhead mechanical stirrer under nitrogen, the flask is charged with 1-propanol (1.0 L), potassium carbonate (45.0 g, 0.33 mol), 3-(but-2-enyloxymethyl)-4-iodo-2-methoxypyridine (Intermediate 2, 49.41 g, 0.16 mol), and palladium (II) acetate (1.42 g, 6.33 mmol). The resulting slurry is heated at reflux for approximately 2 hours. During this time the color of the reaction mixture turns dark brown then light gray. A 150 mL aliquot of the reaction mixture is removed to identify 4-ethylidene-8-methoxy-3,4-dihydro-1H-pyrano[3,4-c]pyridine and 4-ethyl-8-methoxy-1H-pyrano[3,4-c]pyridine.

This aliquot is diluted with 200 mL of tert-butyl methyl ether, filtered, and concentrated in vacuo affording a colorless oil. Chromatography on silica gel (5% ethyl acetate: hexanes) yields 4-ethyl-8-methoxy-1H-pyrano[3,4-c] pyridine. $^1$H-NMR (400 MHz, CDCl$_3$) d 8.04 (d, J=5.4 Hz, 1H), 6.65 (d, J=5.4 Hz, 1H), 6.54 (s, 1H), 5.04 (s, 2H), 3.94 (s, 3H), 2.32 (m, 2H), 0.97 (t, J=7.2 Hz, 3H), HRMS (EI$^+$): calc for $C_{11}H_{13}NO_2$: 191.0946, Found: 191.0952. IR(neat) 3450, 2962, 1731, 1602, 1581, 1454, 1390, 1362, 1313, 1267 cm$^{-1}$. Further elution gives 4-ethylidene-8-methoxy-3,4-dihydro-1H-pyrano[3,4-c]pyridine: $^1$H-NMR (400 MHz, CDCl$_3$) d 7.97 (d, J=6 Hz, 1H), 7.04 (d, J=6 Hz, 1H), 6.33 (q, J=7 Hz, 1H), 4.68 (s, 2H), 4.48 (s, 2H), 3.94 (s, 3H), 1.82 (d, J=2 Hz, 3H); MS (EI) 191 (M$^+$).

The reaction mixture is further treated with potassium ferricyanide (130 g, 0.40 mol), potassium carbonate (55.4 g, 0.40 mol), 2,5-diphenyl-4,6-bis(9-O-dihydroquinidyl) pyrimidine (1.16 g, 1.32 mmol), water (0.85 L) and methane sulfonamide (12.5 g, 0.13 mol). After cooling the mixture to 0° C., potassium (VI) osmate dihydrate (97 mg, 0.26 mmol) is added and the mixture is stirred for 2 days at 0° C.

A 300 ml aliquot of the reaction mixture is removed for identification of 3(R)-4(S)-4-ethyl-8-methoxy-3,4-dihydro-1H-pyrano[3,4-c]pyridine-3,4-diol. The aliquot is diluted with 150 mL of water and extracted with 3×50 mL of methylene chloride. The combined organic layers are washed with 2 N potassium hydroxide. The aqueous layer is extracted with 100 mL of methylene chloride. The combined organic extracts are dried over sodium sulfate, filtered, and concentrated in vacuo giving a crude product. Chromatography of this material on silica gel using 5% methanol:methylene chloride provides an analytical sample of 3(R)-4 (S)-4-ethyl-8-methoxy-3,4-dihydro-1H-pyrano[3,4-c] pyridine-3,4-diol: mp. 106–107° C. (dec); $^1$H-NMR (400 MHz, CDCl$_3$) d 8.11 (d, J=5 Hz, 1H), 7.14 (d, J=5 Hz, 1H), 5.21 (d, J=5 Hz, 1H), 4.84 (d, J=16 Hz, 1H), 4.66 (d, J=16 Hz, 1H), 3.98 (s, 3H), 3.67 (d, J=5 Hz, 1H), 2.60 (s, 1H), 1.87 (q, J=8 Hz, 2H), 0.93 (t, J=8 Hz, 3H); IR 3450, 2948, 2375, 2360, 1604, 1580, 1459, 1403, 1368, 1267 cm$^{-1}$;

Calculated for $C_{11}H_{14}NO_4$: 58.66% C, 6.71% H, 6.22% N; Found 58.75% C, 6.75% H, 6.26% N; $[a]_D^{22}$=−59.2 [c. 0.62, $CHCl_3$].

The reaction mixture is further treated with iodine (280 g, 1.10 mol) and calcium carbonate (54 g, 0.54 mol ) and allowed to stir 2 days at about 22° C. The reaction mixture is cooled to 0° C. and sodium sulfite (150 g, 1.19 mol) is added. After filtering the slurry through Celite 545® the filtrate is extracted with methylene chloride (3×200 mL) and the combined extracts are washed with brine. The organic phase is dried with sodium sulfate and then concentrated to an oil. The crude material is chromatographed (silica gel, 3% methanol/methylene chloride) to yield 4(S)-4-ethyl-4-hydroxy-8-methoxy-1,4-dihydro-pyrano[3,4-c]pyridin-3-one (Intermediate 3) as amber colored oil: $^1$H-NMR (400 MHz, $CDCl_3$) d 8.21 (d, J=5 Hz, 1H), 7.16 (d, J=5 Hz, 1H), 5.58 (d, J=16 Hz, 1H), 5.27 (d, J=16 Hz, 1H), 3.99 (s, 3H), 3.62 (s, 1H), 1.80 (m, 2H), 0.96 (t, J=7 Hz, 3H); Calculated for $C_{11}H_{13}NO_4$: C 59.19, H 5.87, N 6.27; Found: C 59.11, H 5.91, N 6.16; IR (neat) 3480, 2977, 2952, 2360, 1744, 1603, 1592, 1457, 1378, 1379 $cm^{-1}$; $[a]_D^{22}$+85.97°[c 0.677, $CHCl_3$]. Optical purity is determined to be a S/R ration of 10:1 by chiral HPLC: 3% ethanol/hexane, 26° C., 1 mL/min., I=300 nm, Chiralcel-OD column 250×4.6 mm. i.d.

Intermediate 4
1-(7-Amino-2,3-dihydro-benzo[1,4]dioxin-6-yl)-2-chloro-ethanone (Formula (VII))

A 4-necked 12-L round-bottom flask is equipped with a mechanical stirrer and water-cooled condenser. Under nitrogen, the flask is charged with 1 M boron trichloride in methylene chloride (4 L, 4.00 mol). The solution is cooled to −20° C., then 1,4-benzodioxane-6-amine (500 g, 3.31 mol) available from the Aldrich Chemical Company, Inc., 1001 West Saint Paul Avenue, Milwaukee, Wis. 53233, is added as a solution in methylene chloride (250 mL) over 30 min. The temperature increases to 10° C. during the addition and is subsequently re-cooled back to −10° C. Chloroacetonitrile (250 mL, 3.95 mol) is added over 5 min, followed by addition of aluminum chloride (485 g, 3.64 mol). The resulting dark mixture is heated at reflux for 24 h. The reaction mixture is cooled to ambient temperature and transferred to two 20-L separatory funnels, each containing 10 L of water. After being stirred for 2.5 h, the organic layer is separated and the aqueous layer is extracted with methylene chloride (4×4 L). The combined organic layers are washed with brine (4 L), dried over anhydrous sodium sulfate and concentrated in vacuo. The resultant thick brown slurry is successively treated with 600 mL of methylene chloride and 2 L of hexane. The mixture is stirred at 0° C. for 30 min. The precipitate is collected by filtration on a Buchner funnel, washed with hexane (1 L) and dried in vacuo at 30° C. yielding 1-(7-amino-2,3-dihydro-benzo[1,4]dioxin-6-yl)-2-chloro-ethanone as a yellow powder. Reverse HPLC (Spherisorb ODS-25 micron, 1:1 MeCN-$H_2O$) indicated a purity of 91%. Recrystallization from $CH_2Cl_2$ provides an analytical sample as a yellow crystalline solid: mp 130° C. (dec.). $^1$H NMR ($CDCl_3$, 200 MHz) d 4.24 (m, 2H), 4.32 (m, 2H), 4.59 (s, 2H), 6.21 (s, 1H), 6.23 (br. s, 2H), 7.29 (s, 1H). Elemental analysis: Calculated for $C_{10}H_{10}ClNO_3$: C 52.76, H 4.43, N 6.15. Found: C 52.62, H 4.42, N 6.12.

Intermediate 5
9-Chloromethyl-7-oxo-2,3,6,7-tetrahydro[1,4]dioxino[2,3-g]quinoline-8-carboxylic Acid Methyl Ester (Formula (VI))

A 4-necked 12-L round-bottom flask is equipped with a mechanical stirrer and 500-mL addition funnel. Under nitrogen, the flask is charged with 1-(7-amino-2,3-dihydro-benzol[1,4]dioxin-6-yl)-2-chloro-ethanone (Intermediate 4, 595 g, 2.61 mol), triethylamine (474 mL, 3.40 mol), and anhydrous acetonitrile (3.5 L). The solution is cooled to 0° C., then methyl malonyl chloride (364 mL, 3.40 mol) is added over 35 min. The cooling bath is removed and the mixture is stirred for 5 h. To the resultant slurry is added 25% sodium methoxide in methanol (596 mL, 2.61 mol) over 10 min. After being stirred at ambient temperature for 2 h, the now very thick yellow slurry is diluted with water (3 L). The precipitate is collected on a Buchner funnel and washed with water (3 L). The yellow solid is dried in vacuo at 60° C. yielding 9-chloromethyl-7-oxo-2.3,6,7-tetrahydro[1,4]dioxino[2,3-g]quinoline-8-carboxylic acid methyl ester as a yellow solid. This crude product is used for the next step without further purification. Recrystallization from MeOH-DMSO (1:1) gave an analytical sample: mp>300° C. (dec.). $^1$H NMR (DMSO-d6, 400 MHz) d 3.85 (s, 3H), 4.32 (s, 2H), 4.36 (s, 2H), 4.83 (s, 2H), 6.83 (s, 1H), 7.40 (s, 2H), 12.0 (s, 1H). Elemental analysis: Calculated for $C_{10}H_{10}ClNO_3$: C 54.29, H 3.91, N 4.52. Found: C 53.68, H 3.84, N 4.48. HRMS (EI+): Calculated for $C_{10}H_{10}ClNO_3$: 309.0404. Found: 309.0405.

Intermediate 6
7-Chloro-9-chloromethyl-2,3-dihydro[1,4]dioxino[2,3-g]quinoline-8-carboxylic Acid Methyl Ester (Formula (V))

A 4-necked 5-L round-bottom flask is equipped with a mechanical stirrer and water-cooled condenser. Under nitrogen, the flask is charged with 9-chloromethyl-7-oxo-2,3,6,7-tetrahydro[1,4]dioxino[2,3-g]quinoline-8-carboxylic acid methyl ester (Intermediate 5, 360 g, 1.16 mol), as a suspension in phosphorus oxychloride (1.8 kg). The mixture is heated to reflux Generating a black solution. After being heated at reflux for 20 h, the reaction mixture is allowed to cool to ambient temperature and transferred to a 25-L separatory funnel containing 18 L of ice water. After being stirred vigorously for 1.5 h, the precipitate is collected on a Buchner funnel, washed with water (3 L) and dried in vacuo at 50° C. yielding 7-chloro-9-chloromethyl-2,3-dihydro[1,4]dioxino[2,3-g]quinoline-8-carboxlic acid methyl ester as a dark crystalline solid: mp 130–132° C. $^1$H NMR ($CDCl_3$, 200 MHz) d 4.05 (s, 3H), 4.42 (s, 4H), 4.81 (s, 2H), 7.50 (s, 2H). Elemental analysis: Calculated for $C_{14}H_{11}Cl_2NO_4$: C 51.24, H 3.38, N 4.27. Found: C 51.10, H 3.34, N 4.33.

Intermediate 7
7-Chloro-9-(4-methylpiperazin-1-ylmethyl)-2.3-dihydro[1,4]dioxino[2,3-g]quinoline-8Acid Methyl Ester (Formula (IV))

A 4-necked 5-L round-bottom flask is equipped with a mechanical stirrer and 250-mL addition funnel. Under nitrogen, the flask is charged with 7-chloro-9-chloromethyl-2,3-dihydro[1,4]dioxino[2,3-g]quinoline-8-carboxylic acid methyl ester (Intermediate 6, 340 g, 1.04 mol), and methylene chloride (2L). To the stirred solution is added N-methylpiperazine (237 mL, 2.14 mol) over 10 min. After the addition is complete, the reaction mixture is stirred at ambient temperature for 15 h. The reaction mixture is poured into water (3 L) and the organic layer is separated. The aqueous layer is extracted with methylene chloride (3×2 L). The combined organic layers are washed with brine (2 L), dried over anhydrous sodium sulfate and concentrated in vacuo. The resultant thick brown slurry is successively treated with methylene chloride (300 mL) and hexane (1.5 L). The mixture is swirled at 0° C. for 30 min. The precipitate is collected on a Buchner funnel, washed with hexane (1 L) and dried in vacuo at 30° C. yielding 7-chloro-9-(4-methylpiperazin-1-ylmethyl)-2,3-dihydro[1,4]dioxino[2,3-g]quinoline-8-carboxylic acid methyl ester as a yellow powder: mp 143° C. $^1$H NMR (CDCl$_3$, 200 MHz) d 2.28 (s, 3H), 2.38-2.49 (m, 8H), 3.81 (s, 2H), 3.96 (s, 3H), 4.59 (s, 2H), 4.40 (s, 4H), 7.45 (s, 1H), 7.65 (s, 1H). Elemental analysis: Calculated for C$_{19}$H$_{22}$ClN$_3$O$_4$: C 58.24, H 5.66, N 10.72. Found: C 58.08, H 5.72, N 10.63.

Intermediate 8

[7-iodo-9-(4-methylpiperazin-1-ylmethyl)-2,3-dihydro-[1,4]dioxino[2,3-g]quinolin-8-yl]-methanol (Formula (III))

A 4-necked 5-L round-bottom flask is equipped with an overhead mechanical stirrer, a water-cooled condenser and nitrogen flow is maintained. The flask is charged with 7-chloro-9-(4-methylpiperazin-1-ylmethyl)-2,3-dihydro[1,4]dioxino [2,3-g]quinoline-8-carboxylic acid methyl ester (Intermediate 7, 194 g, 495 mol), as a solution in 1 L of methylene chloride. To the solution is added 1 M diisobutylaluminum hydride in methylene chloride (2.00 L, 2.00 mol) over, 15 min. The solution is healed to reflux during the addition. The reaction is allowed to cool to ambient temperature and stirred for 4 h. The reaction mixture is transferred to a 15-L separatory tunnel containing a saturated solution of Rochelle's salt (5 L). After being stirred for 2.5 h, the organic layer is separated and the aqueous layer is extracted with methylene chloride (3×2.5 L). The combined organic layers are washed with brine (3 L), dried over anhydrous sodium sulfate and concentrated in vacuo. The resultant thick brown slurry is successively treated with methylene chloride (500 mL) and hexane (1 L). The mixture is swirled at 0° C. for 30 min. The precipitate is collected on a Buchner funnel, washed with 1 liter of hexane and dried in vacuo. at 30° C. yielding [7-chloro-9-(4-methylpiperazin-1-ylmethyl)-2,3-dihydro-[1,4]dioxino[2,3-g]quinolin-8yl]-methanol as a yellow crystalline solid: mp 178–180° C. $^1$H NMR (CDCl$_3$, 200 MHz) d 2.26 (s, 3H), 2.63 (br. s, 4H), 4.00 (s, 2H). 4.39 (s, 4H), 4.93 (s, 2H), 6.10 (br. s, 1H), 7.46 (s, 1H), 7.51 (s, 1H). Elemental analysis: Calculated for C$_{18}$H$_{22}$ClN$_3$O$_3$: C 59.42, H 6.09, N 11.55. Found: C 59.41, H 6.12, N 11.46.

A 3-necked 4-L round-bottom flask is equipped with a mechanical stirrer and a 250-mL addition funnel. Under nitrogen, the flask is charged with methylene chloride (800 mL), followed by addition of oxalyl chloride (28.8 mL, 330 mmol). The solution is cooled to −78° C. arid dimethyl sulfoxide (46.7 mL, 660 mmol) is added over 6 min. The temperature of the solution increases to −58° C. during the addition and is cooled back to about −70° C. After stirring for 3 min, [7-chloro-9-(4-methylpiperazin-1-ylmethyl)-2,3-dihydro-[1,4]dioxino[2,3-g]quinolin-8-methanol (100 g, 275 mmol), as prepared above, is added as a solution in 140 mL of methylene chloride over 10 min. The yellow slurry is stirred for 45 min, then anhydrous triethylamine (153 mL, 1.10 mol) is added over 4 min. Stirring is continued for 10 min at −78° C., then the cooling bath is removed. The reaction mixture is allowed to warm to −5° C. and poured into 2 L of water. The organic layer is separated and the aqueous layer is extracted with methylene chloride (3×1.5 L). The combined organic layers are washed with brine (2 L), dried over anhydrous sodium sulfate and concentrated in vacuo yielding 7-chloro-9-(4-methylpiperazin-1-ylmethyl)-2,3-dihydro-[1,4]dioxino[2,3-g]quinolin-8-carbaldehyde as a dark solid. This crude product is used for the next step without further purification. Recrystallization from CH$_2$Cl$_2$-MeOH (5:1) provided an analytical sample as a light yellow solid: 140–142° C. (dec.). $^1$H NMR (CDCl$_3$, 200 MHz) d 2.30 (s, 3H), 2.45, 2.59 (m, 8H) 3.98 (s, 2H). 4.41 (s, 4H), 7.46 (s, 1H), 7.53 (s, 1H), 10.4 (s, 1H). Elemental analysis: Calculated for C$_{18}$H$_{20}$ClN$_3$O$_3$: C 59.75, H 5.57, N 11.61. Found: C 59.78, H 5.62, N 11.64.

A 4-necked 12-L round-bottom flask is equipped with a mechanical stirrer and water-cooled condenser. Under nitrogen, the flask is charged with 7-chloro-9-(4-methylpiperazin-1-ylmethyl)-2,3-dihydro-[1,4]dioxino[2,3-g]quinolin-8-carbaldehyde (120 g, 346 mmol), as prepared above, sodium iodide (1.04 kg, 6.92 mmol), and 3 L of acetonitrile. To the yellow suspension is added concentrated hydrogen chloride (59.7 mL, 726 mmol) over 5 min. The white slurry is refluxed for 15 hours. The solvent is mostly removed by short-path distillation in vacuo.

The resultant thick slurry is cooled to ambient temperature and treated with 2.5 L of water and 2.5 L of methylene chloride. The organic layer is separated and the aqueous layer is extracted with methylene chloride (3×2 L). The combined organic layers are washed with brine (2.5 L), dried over anhydrous sodium sulfate, concentrated and dried in vacuo at 30° C. yielding 7-iodo-9-(4-methylpiperazin-1-ylmethyl)-2,3-dihydro-[1,4]dioxino[2,3-g]quinolin-8-carbaldehyde as a yellow solid. This crude product is used for the next step with out further purification. Recrystallization from CH$_2$Cl$_2$—MeOH (1:1) gave an analytical sample as an off-white solid: 198–200° C. (dec.). $^1$H NMR (CDCl$_3$, 200 MHz) d 2.30 (s, 3H), 2.43, 2.57 (m, 8H), 3.93 (s, 2H). 4.40 (s, 4H), 7.47 (s, 1H), 7.50 (s, 1H), 10.1 (s, 1H). Elemental analysis: Calculated for C$_{18}$H$_{20}$IN$_3$O$_3$: C 47.70, H 4.45, N 9.27. Found: C 47.78, H 4.45, N 9.26.

A 3-necked 2-L round-bottom flask is equipped with an overhead mechanical stirrer and nitrogen flow is maintained. The flask is charged with 7-iodo-9-(4-methylpiperazin-1-ylmethyl)-2,3-dihydro-[1,4]dioxino[2,3-g]quinolin-8-carbaldehyde (105 g, 232 mmol), as prepared above, as a suspension in 700 mL of methanol. The mixture is cooled to 0° C., then sodium borohydride (8.76 mmol) is added in three portions over 15 min. The mixture is allowed to warm to ambient temperature and stirred for 2 hours. The solvent is mostly removed in vacuo and the resultant residue is treated with 2.5 L of water and extracted with methylene chloride (4×1.5 L). The combined organic layers are washed with brine (2.5 L), dried over anhydrous sodium sulfate, filtered, and concentrated in vacuo. The resultant solid residue is successively treated with 300 mL of methylene chloride and 300 mL of MeOH-EtOAc (1:1). The mixture is swirled at 0° C. for 30 min. The precipitate is filtered by suction, washed with 500 mL of hexane and dried in vacuo at 30° C. yielding [7-iodo-9-(4-methylpiperazin-1-ylmethyl)-2,3-dihydro-[1,4]dioxino[2,3-g]quinolin-8-yl]-methanol as an off-white powder: mp 201–203° C. (dec.). $^1$H NMR (CDCl$_3$, 200 MHz): d 2.26 (s, 3H), 2.62 (m, 8H), 4.02 (s, 2H). 4.39 (s, 4H), 4.93 (m, 2H), 6.05 (br. s, 1H), 7.49 (s, 1H), 7.51 (s, 1H). HRMS (EI+): Calculated for C$_{18}$H$_{22}$N$_3$O$_3$: 455.0706. Found: 455.0699.

Intermediate 9

4(S)-4-Ethyl-4-hydroxy-4,7-dihydro-1H-pyrano[3,4-c]pyridin-3,8-dione (Formula (IX))

A 1-liter 3-necked round bottom flask is equipped with an overhead mechanical stirrer and a condenser, under nitrogen, the flask is charged with 1 N hydrochloric acid (600 mL) and 101 g of crude 4(S)-4-ethyl-4-hydroxy-8-methoxy-1,4-dihydro-pyrano[3,4-c]pyridin-3-one (Intermediate 3). The resulting solution is heated at reflux for 14 hours. The reaction mixture is cooled to ambient temperature and then concentrated to a solid. The solids are recrystallized in methanol (75 mL) yielding 4(S)-4-ethyl-4-hydroxy-4,7-dihydro-1H-pyrano[3,4-c]pyridin-3,8-dione. mp 224–226° C.; $^1$H-NMR (400 MHz, DMSO-d6) d 11.85 (s, 1H), 7.44 (d, J=7 Hz, 1H) 6.36 (d, J=7 Hz, 1H), 6.28 (s, 1H), 5.24 (s, 2H), 3.36 (s, 3H), 2.99 (s, 1H), 1.75 (m, 2H), 0.81 (t, J=7 Hz, 3H); Calculated for C10H11NO4; C 57.4%, H 5.30%, N 6.70%: Found; C 56.59%, H 5.26%, N 6.66%; MS (EI) 209 (M+); $[a]D^{22}$+115.49° [c 0.877, MeOH]; Optical purity determined by chiral HPLC: 10% ethanol/hexane, 26° C., 1 mL/min., I=300 nm, Chiralcel-OD column 250×4.6 mm. i.d.

Intermediate 10

7-Bromo-9-bromomethyl-2.3-dihydro[1,4]dioxino[2,3-g]quinoline-8-carboxylic Acid Methyl Ester Hydrobromic Acid Salt (Formula (V))

To a mixture of 9-chloromethyl-7-oxo-2,3,6,7-tetrahydro[1,4]dioxinol[2,3-g]quinoline-8-carboxylic acid methyl ester (Intermediate 5, 25 g), in 1,2-dichloroethane (DCE, 90 mL) is added a solution of phosphorus oxybromide (44 g, 2 eq) in DCE (90 mL). The resultant mixture is heated at reflux for 4.0 h, and then cooled to <15° C. Ethanol (91 mL, 20.0 eq) is added while keeping the temp <20° C. The mixture is then allowed to warm to room temperature and stirred overnight. The mixture is filtered and the solid is washed with DCE (30 mL). The solid is dried under high vacuum (about 1 mm Hg) at room temperature overnight to yield 7-bromo-9-bromomethyl-2,3-dihydro[1,4]dioxino[2,3-g]quinoline-8-carboxylic acid methyl ester hydrobromic acid salt as a yellow solid. HRMS (EI$^+$): calc for $C_{15}H_{13}Br_2NO_4$: 428.9211, Found: 428.9238.

Intermediate 11

[7-Bromo-9-(4-methylpiperazin-1-ylmethyl)-2,3-dihydro-[1,4]dioxino[2,3-g]quinolin-8-yl]-methanol (Formula (III))

To a mixture of 7-bromo-9-bromomethyl-2,3-dihydro[1,4]dioxino[2,3-g]quinoline-8-carboxylic acid methyl ester hydrobromic acid salt (Intermediate 10, 10 g, 19.6 mmol) in dichloromethane (DCM, 100 mL) is added triethylamine (5.4 mL, 39.2 mmol) followed by N-methylpiperazine (2.79 mL, 25.5 mmol). After stirring 30 min, water (50 mL) is added and the mixture is stirred 10 min. The layers are separated and the aqueous phase is extracted with DCM (50 mL). The organic phases are combined and washed with water (2×50 mL). The organic solution is then concentrated to an oil. The oil is diluted with DCM (50 mL) and stirred while diisobutylaluminum hydride (1.0 M in dichloromethane, 53 mL. 53 mmol) is added slowly while keeping the reaction temperature below 30° C. using an ice bath. The reaction is stirred for 10 min and then slowly poured into an aqueous solution (75 mL) saturated with potassium sodium tartrate tetrahydrate (Rochelle's salt). The temperature is kept <30° C. with an ice bath during the addition. The mixture gels and is stirred overnight at room temperature. The layers are separated and the aqueous phase is extracted with DCM (2×75 mL). The organics are combined and washed with water (2×50 mL). i he organic phase is then concentrated under vacuum (crystallization occurs during concentration) to about 20 mL and the rest of the product crystallized out by adding tert-butyl methyl ether. The slurry is filtered and dried on high vacuum at room temperature overnight to provide 6.87 g (86%) of [7-bromo-9-(4-methyl-piperazin-1-ylmethyl)-2,3-dihydro-[1,4]dioxino[2,3g]quinolin-8-yl]-methanol as a tan solid.

Intermediate 12

1-(7-amino-2,3-dihydro-benzo[1,4]dioxin-6-yl)-2-chloro-ethanone (Formula VII)

1,4-benzodioxan-6-amine, Formula VIII, (160 g, 1.06 mol) is dissolved in dichloromethane (DCM, 2.4 L) and cooled in an ice bath to less than 10° C. Boron trichloride gas (150 g, 1.27 mol, 1.2 eq) is added over 0.75 hour. The resulting brown slurry is then stirred overnight at room temperature. The slurry is then cooled in an ice bath to 10° C. and chloroacetonitrile (94 mL, 1.48 mol. 1.4 eq) is added in one portion. Gallium chloride (205 g, 1,16 mol. 1.1 eq) is dissolved in DCM (310 mL) and added to the reaction over 0.5 h. The resulting brown slurry is then heated at reflux overnight (13–24 h). The brown solution is then cooled to rt and poured into a stirred mixture or DCM (6.4 L)) and water (6.4 L). The mixture is stirred for 1.5 to 2 h to allow the solids to dissolve. The layers are then separated and the aqueous phase is extracted with DCM (2 L). The organic layers are combined and concentrated under vacuum (about 100 mm Hg) to about 320 mL. (Crystallization occurs during the concentration.) Heptane (640 mL) is added over 1 hour and the slurry stirred overnight at room temperature. The slurry is filtered, washing the cake with heptane (200 mL). The cake is then dried overnight at 40° C. under high vacuum (about 1 mm Hg) to give 206 g (86%) of 1-(7-amino-2,3-dihydro-benzo[1,4]dioxin-6-yl)-2-chloro-ethanone as a yellow solid.

Intermediate 13

9-chloromethyl-7-oxo-2,3,6,7-tetrahydro[1.4]dioxino[2,3-g]quinoline-8-carboxylic Acid Ethyl Ester Formula (VI)

To a mixture of 1-(7-amino-2,3-dihydro-benzo[1,4]dioxin-6-yl)-2-chloro-ethanone (230 g. 1.01 mol) prepared as described in Intermediate 12, in acetonitrile (1.5 L) and triethylamine (197 mL, 1.41 mol, 1.4 eq) is added ethyl malonyl chloride (180 mL, 1.41 mol, 1.4 eq) over 0.5 h while keeping the reaction temperature less than 30° C. with an ice bath. After the addition is complete the reaction is stirred 1.5 h at room temperature. A second charge of Triethylamine (140 mL, 1.01 mol, 1.0 eq) is added and the reaction is stirred for 4.5 hours. Water (2.1 L) is added slowly followed by conc. HCl (115 mL). The slurry is stirred overnight at rt, filtered, and the solid washed with water (460 mL). The solid is then dried under high vacuum (about 1 mm Hg) at 40° C. to give 270 g (83%) 9-chloromethyl-7-oxo-2,3,6,7-tetrahydro[1,4]dioxino[2,3-g]quinoline-8-carboxylic acid ethyl ester as a yellow solid. HRMS (EI$^+$): calc for $C_{15}H_{14}NO_5Cl$: 323.0561, Found: 323.0556.

Example 1

4(S)-4-Ethyl-4-hydroxy-7-[17-iodo-9-(4-methylpiperazin-1-ylmethyl)-2,3-dihydro-[1,4]dioxino]2,3g]quinolin-8-methyl]-dihydro-1H-pyranol[3,4c]pyridine-3,8dione (Formula II))

A 4-necked 2-L round-bottom flask is equipped with mechanical stirrer, and water cooled condenser. Under nitrogen, the flask is charged with 4(S)-4-ethyl-4-hydroxy-4,7-dihydro-1H-pyrano-[3,4-c]-pyridin-3,8-dione (Intermediate 9, 26.7 g, 128 mmol), [7-iodo-9-(4-methylpiperazin-1-ylmethyl)-2,3-dihydro-[1,4]dioxino[]2,3g]quinolin-8yl]-methanol (Intermediate 8, 58.1 g, 128 mmol), triphenylphosphine (33.5 g, 128 mmol) and 318 mL of methylene chloride. The suspension is stirred for 15 min, then diethyl azodicarboxylate (20.1 mL, 128 mmol) is added dropwise over 15 min. During the addition, gentle reflux of the solvent is observed. The brown solution is allowed to cool to ambient temperature and stirred for 6.5 h. The solvent is removed in vacuo. and the resulting residue is treated with 400 mL of benzene and swirled for 3 min. The formed precipitate is filtered by suction and washed with 50 mL of cold benzene. The filtrate is concentrated and the resultant solid is chromatographed on silica gel. Elution with 3-50% MeOH in $CHCl_3$ affords a light yellow solid, which is dissolved in 500 mL MeOH/$CH_2Cl_2$ (1:100). Recrystallization is then initiated by addition of ethyl acetate and filtration by suction and drying in vacuo . The filtrate from the recrystallization is partially concentrated and a second recrystallization is performed. A third recrystallization in the same fashion yields 4(S)-4-ethyl-4-hydroxy-7-[7-iodo-9-(4-methylpiperazin-1-ylmethyl)-2,3-dihydro-[1,4]dioxino[2,3-g]quinolin-8-methyl]-4,7-dihydro-1H-pyrano[3,4-c]pyridine-3,8-dione slightly contaminated with ethyl acetate: mp 158–163° C. (dec.). $[a]_D$=+1.9° (MeOH, c 1.29). $^1$H NMR (CDCl$_3$, 200 MHz) d 0.98 (t, J=7.3 Hz, 3H), 1.83 (q, J=7.3 Hz, 2H), 2.19 (s, 3H), 2.15–2.49 (m, 9H), 3.54 (m, 2H), 4.42 (m, 4H), 5.46 (ABq, J$_{AB}$=15.4 Hz, Dn=94.4 Hz, 2H), 5.51 (ABq, J$_{AB}$=16.3 Hz, Dn=110, Hz, 2H), 6.48 (d, J=7.2 Hz, 1H), 7.20 (d, J=7.2 Hz, 1H), 7.38 (s, 1H), 7.40 (s, 1H). HRMS (EI+): Calculated for C$_{28}$H$_{31}$IN$_4$O$_6$: 646.1239 Found: 646.1304.

Example 2
7-(4-Methylpiperazinomethylene)-10,11-ethylenedioxy-20 (S)-camptothecin (Formula (I))

A 4-necked 3-L round bottom flask is equipped with mechanical stirrer, and water-cooled condenser. Under nitrogen, the flask is charged with 4(S)-4-ethyl-4-hydroxy-7-[7-iodo-9-(4-methyl-piperazin-1-ylmethyl)-2,3-dihydro-[1,4]dioxino[2,3-g]quinolin-8-methyl]-4,7-dihydro-1H-pyrano[3,4c]pyridine-3,8-dione (30.0 g, 46.4 mmol), as prepared in Example 1, palladium acetate (213 mg, 0.928 mmol), anhydrous potassium carbonate powder (12.8 g, 92.8 mmol), triphenylphosphine (6.09 g, 23.2 mmol) and anhydrous acetonitrile (1.8 L). The suspension is brought to reflux during which time the solids dissolve. As the reflux is continued for 16 hours, the product precipitates. The reaction mixture is cooled to 0° C. and stirred for an additional 2.5 hours. The precipitate is collected on a fritted funnel and the resulting yellow cake is treated with 1 L of chloroform. The suspension is filtered and washed with chloroform (5×200 mL), the combined filtrates are concentrated to 300 mL and treated with 30.0 g of triphenylphosphine. After being stirred at ambient temperature for 30 min, the solution is treated with 100 mL of acetone. The resulting precipitate is filtered by suction yields 7-(4-methylpiperazinomethylene)-10,11-ethylenedioxy-20(S)-camptothecin as a light yellow powder. The product is further purified by stirring as a solution in 220 mL of MeOH/CHCl$_3$ (1:10) containing 5.6 g of triphenylphosphine, followed by precipitation with 50 mL of acetone. The precipitate is collected on a Buchner funnel and dried in vacuo. At this stage, analysis shows palladium and phosphorus. Further purification is carried out by dissolving the compound in 165 mL of MeOH/CHCl$_3$ (1:10), followed by precipitation with 150 mL of acetone; filtration and drying in vacuo at ambient temperature. Analysis indicated nondetectable amount (<2 ppm) of palladium and phosphorus in the product: mp: 275° C. (dec.). $[a]_D$=+22.6° (CHCl$_3$, c 1.02). $^1$H NMR (CDCl$_3$, 400 MHz): d 1.04 (t, J=7.4 Hz, 3H), 1.87 (m, 2H), 2.31 (s, 3H), 2.20–2.59 (m, 9H), 3.97 (s, 2H), 4.46 (s, 4H), 5.32 (s, 2H), 5.55 (ABq, J$_{AB}$=16.2 Hz, Dn=180 Hz, 2H), 7.60 (s, 1H), 7.66 (s, 1H), 7.72 (s, 1H). Elemental analysis: Calculated for C$_{28}$H$_{30}$N$_4$O$_6$: C 64.85, H 5.83, N 10.80. Found: C 64.34, H 5.83, N 10.71.

Example 3
7-(4-Methylpiperazinomethylene)-10,11-ethylenedioxy-20 (S)-camptothecin dihydrochloride (Formula (I))

A four-necked 1-L round-bottom Task is equipped with a mechanical stirrer and water cooled condenser. Under nitrogen, the flask is charged with free base 7-(4-methylpiperazinomethylene)-10,11-ethylenedioxy-20(S)-camptothecin (14.0 g, 27.0 mmol), as prepared in Example 2, and 350 mL of 6 N HCl. The suspension is brought to reflux for 35 min. A small amount of precipitate is generated after initial complete solution formation. Without being cooled, the mixture is filtered through a Supor (0.45m) filtering membrane. Washing with hot 6N HCl (100 mL) dissolves the above precipitate. The combined filtrates are cooled to 35° C. Recrystallization is initiated by addition of 20 mL of 200 proof ethanol. After stirring for 1 hour, 150 mL more ethanol is added. The mixture is allowed to stand at 0° C. for 24 h. Filtration and drying in vacuo. at 70° C. yields 7-(4-methylpiperazinomethylene)-10,11-ethylenedioxy-20 (S)-camptothecin dihydrochloride as a yellow powder. A $^1$H NMR shift study with Eu(hfc)$_3$ indicates a single enantiomer. mp 280° C. (dec.). $[a]_D$=−6.72° (H$_2$O, c 0.67). $^1$H NMR (D$_2$O, 400 MHz) d 0.92 (t, J=7.2 Hz, 3H), 1.89 (m, 2H), 2.55 (m, 2H), 2.81 (s, 3H), 2.96 (m, 2H), 3.11 (m, 2H), 3.41 (m, 3H), 3.71 (s, 2H), 5.32 (ABq, J$_{AB}$=16.1 Hz, Dn=54.2 Hz, 2H), 6.84 (s, 1H), 6.97 (s, 1H), 7.00 (s, 1H). Elemental analysis: Calculated for C$_{28}$H$_{30}$N$_4$O$_6$.2HCl.H$_2$O: C 55.18, H 5.62, N 9.19, Cl 11.63. Found: C 55.41, H 5.70, N 9.24, Cl 11.52.

Example 4
4(S)-4-Ethyl-4-hydroxy-7-[7-bromo-9-(4-methylpiperazin-1-ylmethyl)-2,3-dihydro-[1,4]dioxino[2,3-quinolin-8-ylmethyl]-4,7-dihydro-1H-pyrano[3,4-c]pyridine-3,8-dione (Formula II))

To a mixture of 4(S)-4-ethyl-4-hydroxy-4,7-dihydro-1H-pyrano[3,4-c]pyridin-3,8-dione (Intermediate 9, 240g, 1.15 moles), [7-bromo-9-(4-methyl-piperazin-1-ylmethyl)-2,3-dihydro-[1,4]dioxino[2,3g]quinolin-8-yl]-methanol. (Intermediate 13, 609 g, 1.49 moles), and triphenylphosphine (361 g, 1.38 moles) in 2.0 liters of dichloromethane is added diethylazodicarboxylate (217 ml, 1.38 moles) The reaction warms to reflux during the addition. After the addition is complete the mixture is stirred for 50 minutes. The mixture is filtered to remove any solids. To the filtrate is added tert-butyl methyl ether (3.1 liters) with stirring causing a precipitate to form. The resultant mixture is cooled to about 1° C., filtered, and washed with tert-butyl methyl ether. The solid is mixed with 2.9 liters of dichloromethane and 100 mL of methanol, stirred for 15 minutes and filtered. To the filtrate is added with stirring tert-butyl methyl ether (5 L), causing a precipitate to form. The mixture is cooled to 3° C., the solid is collected by filtration, and rinsed with tert-butyl methyl ether. After vacuum drying the solid, obtained 492 g (71%) of 4(S)-4-ethyl-4-hydroxy-7-[7-bromo-9-(4-methyl-1-piperazin-1yl-methyl)-2,3dihydro-[1,4]dioxino[2,3-g]quinolin-8-ylmethyl]-4,7-dihydro-1H-pyrano[3,4-c]pyridine-3,8-dione. MP (183–188° C. (dec.)). HRMS (EI$^+$): calc for C$_{28}$H$_{31}$BrN$_4$O$_6$: 589.1427, Found: 589.1441.

Example 5
7-(4-Methylpiperazinomethylene)-10,11-ethylenedioxy-20 (S)-camptothecin (Formula (I))

After purging with nitrogen, 4(S)-4-ethyl-4-hydroxy-7-[7-bromo-9-(4-methyl-piperazin-1-ylmethyl)-2,3-dihydro-[1,4]dioxino[2,3-g]quinolin-8-ylmethyl]-4,7-dihydro-1H-pyrano[3,4-c]pyridine-3,8-dione (216 g, 0.36 mol) prepared as described in example 4, palladium(II) acetate (4.85 g, 0.0216 mol), powdered potassium carbonate (74.6 g, 0.54 mol), and triphenylphosphine (47.2 g, 0.18 mol) in acetonitrile (9 L) are refluxed under nitrogen for about 12 hours. The mixture is cooled to about 0° C., filtered, and rinsed With acetonitrile (0.2 L). The crude solid is mixed with DCM (3.25 L) and methanol (550 mL), stirred for about 0.5 hours, filtered, and washed with DCM (0.2 L). The filtrate is treated with triphenylphosphine (54 g) and stirred under nitrogen for about 1.5 hours. Acetone (1.9 L) is added (65 ml/min) with stirring, causing a precipitate to form. The mixture is cooled at 0° C. for 4 hours. The mixture is filtered, and the solid is washed with acetone (0.2 L), and air-dried to give crude product (146 g, 78%). The crude product is dissolved in DCM (2.5 L) and methanol (0.3 L) for 0.5 hours. Triphenylphosphine (36.5 g, 0.39 equiv) is added and the solution is stirred at RT for 2.5 hours under nitrogen. Acetone (1.7 L) is added (85 ml/min) causing a precipitate to form. The resulting mixture is cooled at 0° C. for 4 hours. Filtration, washing with acetone (0.4 L), and drying at 30° C. provides crude product (135 g, 72%). The product is dissolved in DCM (2 L) and methanol (0.31 L). Acetone (1.6 L) is added dropwise to the solution causing a precipitate to form. The slurry is cooled at 0° C. for 4 hours. Filtration, washing with acetone (0.2 L), and drying at 30° C. provides crude product (124.8 g, 67%). The crude product is dissolved in DCM (1.6 L) and methanol (350 mL). Acetone (1.4 L) is added (280 ml/min) causing a precipitate to form. The slurry is cooled at 0° C. for 3.5 hours. Filtration, washing with acetone (0.25 vol/wt), and vacuum-drying at 40° C. provides 115 g (61%) of 7-(4-methylpiperazino-methylene)-10,11-ethylenedioxy-20(S)-camptothecin as a yellow solid.

Example 6

4(S)-4-Ethyl-4-hydroxy-7-[7-chloro-9-(4-methylpiperazin-1ylmethyl)-2,3-dihydro-[1,4]dioxino[2,3-g]quinolin-8-ylmethyl]-4,7-dihydro-1H-pyranol[3,4-c]pyridine-3,8-dione (Formula (II))

A mixture of 0.71 g of [7-chloro-9-(4-methyl-piperazin-1-ylmethyl)-2,3-dihydro-[1,4]dioxino[2,3-g]quinolin-8-yl]-methanol, 3.14 mg of 4(S)-4-hydroxy-4,7-dihydro-1H-pyrano[3,4-c]pyridin-3,8-dione, prepared as described in Intermediate 8, above, and 0.47 g of triphenylphosphine is stirred in 2 ml of dichloromethane under nitrogen while 0.28 ml of diethylazodicarboxylate is added dropwise. The mixture is stirred at ambient temperature for 1 hour and the solid is filtered and rinsed with 2 ml of dichloromethane. To the filtrate is added 30 ml of methyl t-butyl ether with stirring. The resulting solid is collected by filtration and rinsed with 4 ml of methyl t-butyl ether to obtained 385 mg of a tan solid. This solid is, dissolved in 2 ml of 10% methanol/dichloromethane to which slowly is added 5.5 ml of methyl t-butyl ether with stirring. After 30 minutes, the slurry is cooled to 0° C. for 30 minutes, the solid is collected by filtration and washed with 5 ml of methyl t-butyl ether. After drying, the yield is 281 mg of 4(S)-4-ethyl-4-hydroxy-7-[7-chloro-9-(4-methyl-piperazin-1-yl-methyl)-2,3-dihydro-[1,4]dioxino[2,3-g]quinolin-8-yl]-4,7-dihydro-1H-pyrano[3,4-c]pyridine-3,8-di-one as an off white solid: m.p. (179-183 (dec.)); mass spectrum m/z=555.32, 557 (40% of 555); IR (film) 1800, 1660, 1620, 1570, 1505 cm-1.

Example 7

7-(4-Methylpiperazinomethylene)-10,11-ethylenedioxy-20(S)-camptothecin (Formula (I))

A mixture of 100 mg of 4(S)-4-ethyl-4-hydroxy-7-[7-chloro-9-(4-methyl-piperazin-1-ylmethyl)-2,3-dihydro-[1,4]dioxano[2,3-g]quinolin-8-yl]-4,7-dihydro-1H-pyrano[3,4-c]pyridine-3,8-dione, 4 mg of palladium acetate, 19 mg of triphenylphosphine, and 37 mg of potassium carbonate in 4 ml of anhydrous acetonitrile is purged with nitrogen and refluxed for 19 hours. When the reaction is 99% complete (as monitored by HPLC), it is cooled and the resulting solid is collected by filtration, washed with 2 ml of acetonitrile, and resuspended in 2 ml of 10% methanol/dichloromethane. The solid is then removed by filtration, and 4 ml of acetone is added with stirring. After 1 hour, the solid is collected by filtration and rinsed with 4 ml of acetone. After drying, the yield is 51 mg (55%) of 7-(4-methylpiperazinomethylene)-10,11-ethylenedioxy-20(S)-camptothecin.

What is claimed is:

1. A process for the preparation of a compound of formula V

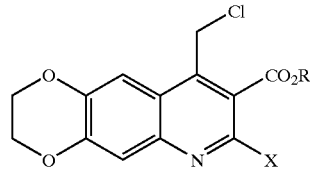

wherein X is halogen and R an alkyl group, comprising:

reacting a compound of formula VI

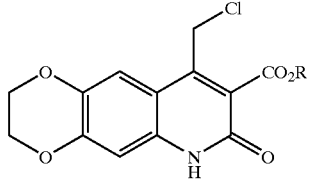

with a halogenating agent in a cosolvent.

2. The process of claim 1, wherein the halogenating agent is phosphorus oxychloride or phosphorus oxybromide.

3. The process of claim 1, wherein the cosolvent is 1,2-dichlorethane.

4. The process of claim 1, wherein the reaction is carried out at a temperature from about 50° C. to about 120° C.

5. The compounds of claim 1, wherein X is chloro or bromo and R is methyl or ethyl.

* * * * *